United States Patent [19]

MacLennan et al.

[11] 3,989,594
[45] Nov. 2, 1976

[54] MICROBIOLOGICAL PRODUCTION OF PROTEIN

[75] Inventors: David Graham MacLennan; John Clark Ousby; Terence Robert Owen; David Charles Steer, all of Stockton-on-Tees, England

[73] Assignee: Imperial Chemical Industries Limited, London, England

[22] Filed: Nov. 15, 1973

[21] Appl. No.: 416,098

Related U.S. Application Data

[63] Continuation of Ser. No. 203,061, Nov. 29, 1971, abandoned.

[30] Foreign Application Priority Data

Dec. 9, 1970 United Kingdom .................... 58466
Aug. 19, 1971 United Kingdom .................... 38938

[52] U.S. Cl. .................................... 195/49; 195/96
[51] Int. Cl.$^2$ ........................................... C12B 1/00
[58] Field of Search ............. 195/49, 96, 28 R, 115; 426/204

[56] References Cited

UNITED STATES PATENTS

| 3,546,071 | 12/1970 | Douros et al. ........................ 195/96 |
| 3,616,224 | 10/1971 | Kamakura et al. .................. 195/49 |
| 3,663,370 | 5/1972 | Kono et al. ........................... 195/49 |

OTHER PUBLICATIONS

Breed, *Bergy's Manual of Classification of Determinative Bacteriology* The Williams & Wilkins Co. p. 277 (1957).
Oki et al., "The Isolation and Growth of Methanol Utilizing Strains of Bacteria—Research for Utilization of Non–glucide Subtrates by Microorganisms; Report No. 5–", preprint of lecture No. 755 presented at annual meeting of the Agr. Chem. Soc. of Japan on 2nd Apr., 1969 in Tokyo.
Kouno et al., "The Classification of Methanol Utilizing Microorganisms" preprint of lecture No. 1H–23 presented at the annual meeting of Agr. Chem. Soc. of Japan on 1st Apr., 1970.
Kouno et al., "Isolation of New Methanol–Utilizing Bacteria and its Thiamine–Requirement for Growth" *J. Gen. Appl. Microbiol.* vol. 19, pp. 11–21 (1973).
Anthony et al., *Biochemical Journal*, vol. 92 p. 609 (1964).
Kaneda et al., *Canadian Journal Microbiology*, vol. 5, p. 87 (1959).
Peel et al., *Biochemical Journal*, vol. 81, p. 465 (1961).

*Primary Examiner*—A. Louis Monacell
*Assistant Examiner*—Thomas G. Wiseman
*Attorney, Agent, or Firm*—Cushman, Darby & Cushman

[57] ABSTRACT

Growth of bacteria belonging to new species of genera *Pseudomonas*, *Microcyclus* and *Hyphomicrobium* upon culture media comprising sources of assimilable carbon, for example oxygenated hydrocarbons, and inorganic nutrients to produce protein compositions and/or other fermentation products, for example amino acids. The protein compositions produced are suitable for use as protein supplements in human and animal foods.

9 Claims, No Drawings

MICROBIOLOGICAL PRODUCTION OF PROTEIN

This is a continuation of application Ser. No. 203,061 filed Nov. 29, 1971, now abandoned.

This invention relates to a process for the microbiological production of protein compositions suitable for use as food supplements for human or animal consumption.

In an attempt to alleviate the present world shortage of protein, several microbiological processes have recently been proposed for producing protein compositions by growing micro-organisms on various carbon-containing substrates. it is desirable that such processes should use inexpensive and readily available carbon-containing substrates, should give a high rate of protein production and that the compositions produced should have a suitable amino acid distribution.

Studies of bacteria have shown that strains of a few species are capable of utilizing methanol as a carbon source for growth. However the proteinaceous products produced by growing these strains upon methanol were not recovered.

We have isolated several methanol utilizing strains of bacteria of species which we believe to be hitherto unknown and which we have named *Pseudomonas methylotropha, Pseudomonas rosea, Microcyclus polymorphum* and *Hyphomicrobium variabile*, which are capable of growing upon methanol to give a high rate of crude protein production and to produce protein compositions having acceptable amino acid contents.

According to the present invention we provide a process for the microbiological production of protein compositions and/or other fermentation products, for example amino acids such as lysine and methionine, which comprises aerobically culturing bacteria belonging to one or more methanol utilizing strains of the species *Pseudomonas methylotropha, Microcyclus polymorphum, Hyphomicrobium variable* and *Pseudomonas rosea*, the characteristics of which species are hereinafter described, in an aqueous culture medium comprising a source of assimilable carbon and inorganic nutrients and recovering the protein compostions and/or other fermentation products produced.

Also according to the invention we provide a proteinaceous product comprising dried cells of bacteria belonging to one or more methanol utilizing strains of the species *Pseudomonas methylotropha, Microcyclus polymorphum, Hyphomicrobium variabile* and *Pseudomonas rosea*, the characteristics of which species are hereinafter described.

Also according to the invention we provide a human or animal food composition comprising one or more foodstuffs and a proteinaceous food supplement comprising dried cells of bacteria belonging to one or more methanol utilizing strains of the species *Pseudomonas methylotropha, Microcyclus polymorphum, Hyphomicrobium variabile* and *Pseudomonas rosea*, the characteristics of which species are hereinafter described.

Also according to the invention we provide methanol utilizing strains of bacteria belonging to the species *Pseudomonas methylotropha, Microcyclus polymorphum Hyphomicrobium variabile* and *Pseudomonas rosea*, the characteristics of which species are hereinafter described.

Representative cultures of suitable strains of the newly isolated species have been deposited with the National Collection of Industrial Bacteria, Torry Research Station, Aberdeen, Scotland, U.K. and have been given the following NCIB Accession numbers:

*Pseudomonas methylotropha* Strains WKM-3, WKM-1, SA, SB, SD, SE, SF, $AS^{-1}$, MP4, F16/1, F16/2, MPI/Sh/37/1 and 28/D/37 — NCIB Nos. 10508–15 and 10592–96 respectively.

*Microcyclus polymorphum* Strain Pla 5 — NCIB No. 10516

*Hyphomicrobium variable* Strain S/30/4 — NCIB No. 10517

*Pseudomonas rosea* Strains MA2/3, BDD/3, MA3D/1, MW4/4, MPID/2, MP3D/2, MP1/2, MA2/2, 20D, MA1/5, MA3D/3, BDD/2, MP1, ChD, WS, MP3 — NCIB Nos. 10597–10612 respectively.

The above strains have also been deposited with the permanent collection of the Northern Utilization & Research Division, Agricultural Research Service, U.S. Department of Agriculture, Peoria, Illinois, and have been given NRRL accession numbers as follows:

NRRL B5352–5364, respectively, for the strains identified above by NCIB Nos. 10508–15 and 10592–96, respectively;

NRRL B5365–5380, respectively, for the strains identified above by NCIB Nos. 10597–10612, respectively;

NRRL B5381 for the strain (Strain Pla 5) identified above by NCIB No. 10516; and NRRL B5382 for the strain (Strain S/30/4) identified above by NCIB No. 10517.

The microbiological characteristics of the newly isolated species as determined by standard microbiological tests are as follows:

A. *Pseudomonas methylotropha*

The general characteristics of this species are:

1. Microscopic morphology (when grown on methanol mineral salts agar plates, or in methanol mineral salts medium) shape - straight rods: length — 0.8–1.5 $\mu$: width —0.3–0.5$\mu$: aggregates — cells occur singly and in pairs: motility — when present by polar flagella: Gram stain — Gram negative, evenly staining but the stain is often not taken up well: Intracellular storage products — poly-$\beta$-hydroxybutyrate is not produced: Endospores — not produced; capsules — not produced: extracellular slime — some produced.

2. Colonial morphology
   a. on methanol mineral salts agar plates incubated for 2 days at 37° C. shape — circular: size — 1–2 mm. diameter: elevation — convex: surface —smooth: edge — entire: texture — granular: density — dense: pigment — greyish-white: consistency — butyrous: emulsifiability — usually difficult to emulsify.
   b. on nutrient agar (2 days at 37° C) — growth is usually very poor, only being visible as a transparent haze or as tiny, pinpoint colonies less than 0.5 mm diameter.

3. Physiological and Biochemical Tests
   a. growth in nutrient both — no growth or very poor growth mainly at the surface.
   b. Gelatin stab — no growth or liquefaction.
   c. Reduction of nitrates — nitrates reduced to nitrites.
   d. Relation to oxygen — aerobic
   e. Indole production — weak positive, faint indole production.
   f. Temperature relations — growth at 4° or 42° C, good growth at 30° and 37° C.

g. Metabolism of carbohydrates (Hugh & Liefson's test) — when growth occurs it is oxidative.
h. Lipase production (hydrolysis of 'Tween 80') — negative.
i. Lecithinase production (egg yolk reaction) — negative.
j. Urease production — variable, usually positive.
k. Hydrogen sulphide production — negative.
l. Citrate utilisation (Kosers citrate test) — negative.
m. Methyl red test — negative
n. Voges — Proskauer test — negative
o. Growth in litmus milk — poor, slight acid production
p. Fluorescein production (Kings medium A) — not produced
q. Pyocyanin production (Kings medium B) — not produced
r. Antibiotic sensitivity — sensitive to chloramphenicol, streptomycin, and tetracyclin, resistant to penicillin, novobiocin and oleandomycin, variable sensitivity to erythromycin and sulphafurazole.
s. Growth on blood agar — slight growth, no haemolysis.
t. Oxidase test (Kovac's) — positive Metabolism of carbon sources - The carbon sources which are utilized by the individual strains of a given species vary to some extent. In the present case most strains have a very restricted nutritional spectrum and do not grow well on many carbon sources. Methanol and fructose are utilized by all strains specifically referred to in this specification. After a period of adaption over several subcultures other carbon sources may be used.

Strains NCIB Nos. 10508–15 and 10592–96 are similar to one another and are believed to be strains of the same species. The general characteristics of these strains are the same as those described for the species, with the following distinguishing features:

Strain WKM-3 (NCIB 10508)

Source — estuarine mud. Utilises acetate, butyrate, propionate, pyruvate, succinate and adipate as sole sources of carbon and energy. Catalase negative, resistant to erythromycin, sensitive to sulphafurazole.

Strain WKM-1 (NCIB 10509)

Source — estuarine mud. Utilises acetate, butyrate, propionate, pyruvate, succinate, glutarate and adipate as sole carbon/energy source. Urease is not produced, catalase negative, resistant to erythromycin and sulphafurazole.

Strain SA (NCIB 10510)

Source — sewage sludge. Resistant to erythromycin and sulphafurazole. Catalase positive.

Strain SB (NCIB 10511)

Source — sewage sludge. Catalase positive, sensitive to erythromycin and sulphafurazole.

Strain SD (NCIB 10512)

Source — sewage sludge. Catalase positive. Resistant to sulphfurazole and erythromycin.

Strain SE (NCIB 10513)

Source — sewage sludge. Catalase positive, sensitive to sulphafurazole and erythromycin.

Strain SF (NCIB 10514)

Source — sewage sludge. Catalase positive, urease negative, sensitive to sulphafurazole resistant to erythromycin.

Strain AS1 (NCIB 10515)

Source — activated sludge. Catalase positive, sensitive to sulphafurazole and erythromycin.

Strain MP4 (NCIB 10592)

Source — stagnant pool of water. Catalase positive, resistant to sulphafurazole and erythromycin.

Strain F16/1 (NCIB 10593)

Source — pond mud. Catalase positive resistant to sulphafurazole and erythromycin.

Strain F16/2 (NCIB 10594)

Source — pond water. Catalose positive resistant to sulphafurazole and erythromycin.

Strain MP1/Sh/37/1 (NCIB 10595)

Source — stagnant pool of water. Catalase negative, resistant to sulphafurazole and erythromycin.

Strain 28/D/37 (NCIB 10596)

Source — river water. Catalase positive, urease negative, sensitive to sulphafurazole and erythromycin.

Similar strains to those described above may be isolated from a variety of different natural sources including soil, decaying vegetation, pond water, and river water. Suitable isolation techniques for obtaining such strains include streaking out on methanol mineral salts agar plates from the sample and picking off appropriate colonies for further purification, or static or shaken enrichments in liquid culture (with or without serial subcultures) in methanol mineral salts medium. Isolation may be performed at temperatures from 25°–45° C, but preferably at 37° C, and at pH values from pH 5.5 to pH 8.0, but preferably from pH 6.5 to pH 7.2.

IDENTITY OF STRAINS NCIB NOS. 10508-15 AND 10592-96

The microbiological characteristics of these strains place them in the genus *Pseudomonas* according to Bergey's Manual of Determinative Bacteriology (7th Edition), editors Breed, Murray & Smith, published by Williams & Wilkins Baltimore 1957. On following through the key to the species of this genus there is no species described in Bergey's Manual having the characteristics described above. No reference to bacteria having similar characteristics has been found in the literature.

Thus it is concluded that these strains of the genus *Pseudomonas* belong to a species not hitherto known. The differences between these strains are sufficiently minor for them to be considered as being strains of the same species (similar variation between strains of a given species are found in other species of the genus *Pseudomonas* as demonstrated by the work of R. T. Stanier, N. V. Palleroni, & M. Dondoroff "The aerobic pseudomonads: a taxonomic study "Journal of General Microbiology 1966 Vol. 43, P. 159). Throughout this specification the new species will be referred to as *Pseudomonas methylotropha*.

B. Microcyclus polymorphum Strain PIa5(NCIB No. 10516)

This micro-organism is very different in microbiological character from *Pseudomonas methylotropha* and from the methanol-using bacteria known in the literature.

1. Microscopic morphology:
   a. methanol mineral salts yeast extract agar plates after 3 days incubation at 37° C: small very curved gram negative rods, which during growth unite at the ends to form closed rings approximately 1.5 microns in diameter. The width of the rods is approximately 0.3–0.5 microns. Also visible are horseshoe-shaped forms which have not united at the ends, and curved rods. Non-motile, no visible storage granules, no spores produced, no capsule or appreciable quantities of slime formed.
   b. nutrient agar — 3 days incubation at 37° C: gram negative rods, somewhat larger than when grown on methanol mineral salts yeast extract agar. The rods are straight or curved, occurrring singly and not generally appearing to form closed rings or horse-shoe shapes.

2. Colonial morphology
   a. on methanol mineral salts agar and yeast extract plates incubated for 2 days at 37° C. Shape — circular: size — less than 1 mm diameter: elevation—convex: surface — smooth: edge — entire: density — translucent: colour — cream: consistency — butyrous: emulsifiability — easily emulsified.
   b. on nutrient agar plates incubated for 2 days at 37° C Shape — circular: size — 1-3 mm diameter: elevation — convex: surface — smooth: edges — entire: density — dense: pigment — cream to brown, non water-soluble: consistency — butyrous: emulsifiability — difficult to emulsify.

3. Physiological and Biochemical Characters.
   a. Growth in nutrient broth — growth fairly homogeneous, with some sediment, but no pellicle.
   b. Gelatin stab — growth but no liquefaction.
   c. Reduction of nitrates — nitrates reduced to nitrites.
   d. Indole production — indole produced (weak positive)
   e. Temperature relations — no growth at 4° or 42° C. Optimum temperature 37° C.
   f. Relation to oxygen — aerobic to facultatively anaerobic.
   g. Metabolism of carbohydrates (Hugh & Leifson's test) — oxidative with some acid produced.
   h. metabolism of various carbon sources — the following carbon sources (of those tested) are utilised by this strain: methanol, ethanol, propanol, acetate, pyruvate, oxalate, succinate, glutarate, sucrose, lactose, glucose, mannitol, ribose, ribitol, xylose, fructose, hexane, hexadecane, serine.
   i. Lipase production (Tween 80 hydrolysis) — negative.
   j. Lecithinase production (egg yolk reaction) — negative.
   k. Urease production — negative.
   l. Hydrogen sulphide production — negative.
   m. Citrate utilisation (Kosers citrate test) — negative.
   n. Methyl red test — negative.
   o. Voges - Proskauer test — negative.
   p. Growth in litmus milk — growth, some alkali produced.
   q. Fluorescein production (Kings medium A) — not produced.
   r. Pyocyanin production (Kings medium B) — not produced.
   s. Antibiotic sensitivity — sensitive to chloramphenicol, stroptomycin and tetracycline, resistant to penicillin, erythromycin, sulphafurazole, novobiocin, and oleandomycin.
   t. Growth on blood agar — growth but no haemolysis.
   u. Oxidase test (Kovac's) — positive.
   v. Catalase test — positive.

4. Source — river mud.

IDENTITY OF STRAIN Pla 5 (NCIB 10516).

The microbiological characteristics of this strain are commensurate with it being a member of the genus *Microcyclus*, according to Bergey's Manual of Determinative Bacteriology. Only one species of this genus is described in Bergey's Manual and strain NCIB 10516 differs from this species in that NCIB 10516 is smaller, grows well at 37° C, and has a growth factor requirement. No reference has been found in the literature to a species of *Microcyclus* possessing characteristics the same as those of strain NCIB 10516. Thus it is concluded that this strain belongs to a species not hitherto known.

Throughout this specification this species will be referred to as *Microcyclus polymorphum*.

C. Hyphomicrobium sp. Strain S/30/4 (NCIB No. 10517)

This micro-organism differs considerably from the strains described above and from bacteria which are known in the literature to use methanol as a carbon source.

1. Microscopic morphology: (7 days growth at 30° C on methanol mineral salts agar plates): Gram variable, short, stout rods with pointed ends. Size 0.6–1.0 microns wide by 1.0–1.5 microns long. Each micro-organism may contain one (or occasionally more) granules of poly-$\beta$-hydroxybutyrate. The rods produce narrow filaments 0.2–0.3 microns wide which vary in length, but at the end of which a daughter cell develops and eventually splits off to form a separate individual.

2. Colonial morphology: (7 days growth) at 30° C on methanol mineral salts agar plates): colonies are small (1-2 mm diameter) circular in shape with an entire margin, convex, smooth, opaque, cream in colour.

3. Physiology
   a. relation to oxygen: aerobic.
   b. temperature relations: optimum temperature 30° C, will grow at 37° C. No growth at 4° or 42° C.
   c. Growth in nutrient broth — growth homogeneous, no pellicle or sediment.
   d. Gelatin stab — growth, but no liquefaction.
   e. Reduction of nitrates — nitrates not reduced to nitrites.
   f. Indole production — indole not produced.
   g. Metabolism of carbohydrates (Hugh & Liefson's test) — oxidative with acid produced.

h. Metabolism of various carbon sources — the following carbon sources of those tested) are utilized: methanol, ethanol, propanol, buthanol, formate, acetate, propionate, butyrate, pyruvate, oxalate, succinate, glutarate, adipate, sucrose, lactose, mannose, mannitol, ribose, ribitol, xylose, fructose, naphthalene, benzoate, hexadecane.

i. Lipase production (Tween 80 hydrolysis) — negative.

j. Lecithinase production (egg yolk reaction) — negative.

k. Urease production — positive.

l. Hydrogen sulphide production — negative.

m. Citrate utilisation (Kosers citrate test) — negative.

n. Methyl red test — negative.

o. Voges-Proskauer test — negative.

p. Growth in litmus milk — growth, alkaline reaction, slight clot.

q. Fluorescein production (Kings medium A) fluorescein not produced.

r. Pyocyanin production (Kings medium B) — pyocyanin not produced.

s. Antibiotic sensitivity — sensitive to penicillin, chloramphenicol, oleandomycin, streptomycin, tetracyclin.

t. Growth on blood agar — growth, but no haemolysis.

u. Oxidase test (Kovacs) — positive v. Catalase test — positive.

4. Source — rotting silage

IDENTITY OF STRAIN NCIB 10517

This organism may be readily identified as a member of the genus *Hyphomicrobium* as described in Bergey's Manual of Determinative Bacteriology, but in view of the difference in size, variable reaction to the Gram stain and other characteristics listed above, this strain differs from the one species described in Bergey's Manual. No reference to a species of *Hyphomicrobium* having the same characteristics as NICB 10517 has been found in the literature. Thus it is concluded that strain NCIB 10517 belongs to a species not hitherto known.

Throughout this specification the new species will be referred to as *Hyphomicrobium variabile*.

D. Pseudomonas rosea

The general characteristics of this species are:

1. Microscopic morphology: of cells grown in MeOH mineral salts medium Large Gram negative straight to slightly curved rods $2-3\mu$ long by $1\mu$ wide, occuring singly. The rods are motile by polar flagella. Poly-B-hydroxybutyrate is produced and is stored intracellularly forming one or more discrete storage granules. Spores, slime and capsules are not evident.

2. Colonial morphology a. on methanol mineral salts agar plates incubated for two days at 37° C. Circular colonies with a convex elevation. Diameter 1–2 mm, edge entire, surface smooth. The colonies are easily emulsified, and the consistency is butyrous. A salmon pink to red non-water soluble pigment is produced.

b. on nutrient agar plates incubated for 2 days at 37° C. The colonial morphology is the same as that described for growth on methaol mineral salts agar, with the exception that the nutrient agar colonies are usually somewhat smaller than methanol mineral salts agar colonies.

3. Physiology a. growth in nutrient broth (after 3 days incubation at 37° C): mainly at the bottom of the tube.

b. gelatin hydrolysis: gelatin is not hydrolysed in 7 days.

c. nitrate reduction: nitrates are not generally reduced to nitrite, although nitrate forms an acceptable nitrogen source.

d. indole production: indole is not produced.

e. temperature relations: optimum temperature 37° C, no growth evident at 4° C in 7 days, growth at 42° C in 7 days.

f. Hugh & Leifson test (glucose as carbon source) — growth oxidative with some alkali produced.

g. Oxidase test — oxidase negative.

h. Catalase test — catalase positive.

i. Methyl red test — negative. resistant j. Voges-Proskauer test — negative.

k. Litmus milk — growth but no acid or alkali produced.

l. Production of fluorescein and pyocyanin in Kings medium (A and B) — growth but no pigment produced.

m. Antibiotic sensitivity (using 'Oxoid' brand 'multodisks') — resistant to penicillin, chloramphenicol, erythromycin, sulphafurazole, novobiocin and oleandomycin; sensitive to streptomycin and tetracyclin.

n. Growth on blood agar — growth but no haemolysis.

o. Lipase production (Tween 80 hydrolysis) — negative.

p. Lecithinase production — variable reaction.

q. Urease production — variable reaction.

r. Hydrogen sulphide production — negative.

s. Citrate utilisation — variable reaction.

Metabolism of carbon sources — some variation occurs between the individual strains but in general the following compounds are utilised as sole carbon/energy sources - methanol, ethanol, propanol, formate, acetate, pyruvate, succinate, glucose, fructose, arginine, serine. The following compounds are not generally utilised as sole carbon/energy sources — butanol, propionate, butyrate, adipate, methylamine, di-methylamine, ethylamine, lactose, mannitol, ribitol, xylose, naphthalene, phenol, benzoate, hexane, aspartate, alanine, glycine.

Strains NCIB Nos. 10597–10612 are similar to one another and are believed to be strains of the same species. The general characteristics of these strains are the same as those described above for the species with the following distinguishing features:

Strain MA2/3 (NCIB 10597)

Grows slowly at 4° C, is sensitive to novobiocin, but not streptomycin, it does not utilise formate, oxalate, mannose or ribose, but does utilise glutarate, citrate sucrose, and glutamate. Source: factory site mud. Lecithinase positive, urease positive.

Strain BDD/3 (NCIB 10598)

Grows slowly at 4° C, is sensitive to sulphafurazole and novobiocin, but not streptomycin or tetracyclin. It does not utilise citrate or pyruvate, but does utilise butanol, oxalate, glutarate, sucrose, mannose, ribose, alanine, glycine and glutamate.

Urease positive, lecithinase negative. Source — chicken dung.

Strain MA3D/1 (NCIB 10599)

Utilises oxalate, glutarate, sucrose, mannose, ribose and glutamate. Lecithinase positive, urease positive. Source — factory site mud: citrate not utilised.

Strain MW4/4 (NCIB 10600)

Grows slowly at 4° C and utilises oxalate, glutarate, sucrose, mannose, ribose, alanine, glycine and glutamate. Lecithinase positive, urease positive, citrate not utilised. Source: from marsh water.

Strain MP1D/2(NCIB 10601)

Grows slowly at 4° C and is sensitive to erythromycin. It does not utilise pyruvate, but does utilise oxalate, citrate, glutarate, sucrose, mannose, ribose, xylose, alanine and glutamate. Lecithinase negative, urease positive. Source: factory site mud.

Strain MP3D/2 (NCIB 10602)

Resistant to tetracyclin, and does not utilise citrate, oxalate, glutarate, sucrose, mannose or glutamate, but does utilise ribose. Lecithinase positive, urease negative. Source: factory site mud.

Strain MP1/2 (NCIB 10603)

Sensitive to streptomycin, does not utilise propanol, formate, oxalate, glutarate, sucrose, mannose, ribose, glutamate or arginine. Lecithinase negative. Urease positive, citrate is utilised. Source: factory site mud.

Strain MA/2/2 (NCIB 10604)

Does not utilise propanol, formate, oxalate, glutarate, sucrose, mannose, ribose, glutamate or arginine. Lecithinase negative, urease negative, citrate is utilised. Source: factory site mud.

Strain 20/D(NCIB 10605).

Sensitive to novobiocin, does not utilise propanol, oxalate, glutarate, mannose or glutamate, but does utilise sucrose, citrate and ribose. Lecithinase negative, urease negative. Source: rotting vegetables.

Strain MA1/5 (NCIB 10606)

Sensitive to erythromycin, does not utilise oxalate, glutarate, sucrose, mannose, ribose, arginine or serine, but does utilise citrate and glutamate. Lecithinase negative, urease negative. Source: factory site mud.

Strain MA3D/3 (NCIB 10607)

Sensitive to penicillin and chloramphenicol, does not utilise butanol, propanol, formate, oxalate, glutarate, sucrose, mannose, glutamate, arginine or serine, but does utilise citrate and ribose. Lecithinase positive, urease positive. Source: factory site mud.

Strain BDD/2 (NCIB 10608)

Sensitive to novobiocin, does not utilise glutarate, mannose or serine, but does utilise oxalate, sucrose, citrate, ribose, alanine and glutamate. Lecithinase negative urease positive. Source: chicken dung

Strain MP1 (NCIB 10609)

This strain does not utilise acetate, glutarate, glutamate, arginine or serine, but does utilise oxalate, citrate, mannose, mannitol, sucrose, ribitol, ribose and xylose. Lecithinase negative, urease negative. Source: factory site mud.

Strain ChD (NCIB 10610)

Sensitive to chloramphenicol, erythromycin, novobiocin and oleandomycin. It does not utilise formate, glutarate, glutamate, arginine or serine, but does utilise citrate, oxalate, sucrose, mannose, mannitol, ribose, ribitol and xylose. Lecithinase negative, urease negative. Source: chicken dung.

Strain WS (NCIB 10611)

Sensitive to novobiocin, does not utilise oxalate, glutarate, arginine, serine or glutamate, but does utilise citrate, sucrose, mannose, mannitol, ribose, ribitol and xylose. Lecithinase positive, urease positive. Source: woodland soil

Strain MP3 (NCIB 10612)

Sensitive to novobiocin, does not utilise ethanol, glutarate, sucrose, mannose, ribose, arginine, serine, or glutamate, but does utilise oxalate, citrate, mannitol and xylose. Lecithinase negative, urease negative. Source: factory site mud.

IDENTITY OF STRAINS NCIB NOS. 10597-10612

The microbiological characteristics of these strains place them in the genus Pseudomonas according to Bergey's Manual of Determinative Bacteriology. On following through the key to the species of these genus there is no species described in Bergey's Manual having the characteristics described above. Similar species are Pseudo monas (Vibrio) extorquens and Protaminobacter ruber. Certain other pink-pigmented methanol-utilising bacteria have been described in the microbiological literature, principally Pseudomonas sp strain AM1 (Peel & Quayle, 1961, Biochem J, 81, 465). It is now generally accepted by workers in this field that Pseudomonas extorquens, Protaminobacter ruber, Pseudomonas sp strain AM1 and other similar known strains of pink-pigmented methanol utilizing bacteria are in reality different strains of the same species (Stocks & McCleskey, 1964, J Bacteriol. 88, 1065).

Strains NCIB 10597–10612 differ characteristically from these known strains on the basis of the following features:

|  | Known Pseudomonas extorquens strains | Strains NCIB 10597–10612 |
| --- | --- | --- |
| Oxidase test | weak +ve | negative |
| Growth at 42° C | No growth | growth |
| Optimum Temperature | 30° C | 37° C |
| Growth on methylamine | growth | no growth |
| Growth on lactose | growth | no growth |
| Grown on naphthalene | growth | no growth |
| Colony size on methanol salts agar (48 hour growth) | <1 mm diameter | 1–2 mm diameter |
| Pigment | Deep pink to red | Salmon to deep rose pink. |

Thus it is concluded that strains 10597–10612 belong to a species hitherto unknown. The differences between these strains are sufficiently minor for them to be considered to be strains of the same species (similar variations between strains of a given species being found in other species of the genus *Pseudomonas* as demonstrated by the work of Stanier et al (hereinbefore referred to).

Throughout this specification the new species will be referred to as *Pseudomonas rosea*.

It is recognised that other strains having the general properties of the four new species described hereinbefore, such that they would be included in these species, but might have slightly different characters from the strains described may be isolated from natural sources. It is intended that the use of such strains, and the use of any mutant strains derived from any member of any of the four species should be included in the scope of the invention. The strains of the invention are capable of growth upon methanol to convert methanolic carbon to cell carbon.

The tests used in the identification of the strains described are as follows:

1. Media

The composition of the methanol mineral salts medium used for the tests was:

| | |
|---|---|
| $KH_2PO_4$ | 1.4 g |
| $Na_2HPO_4$ | 2.1 g |
| $(NH_4)_2SO_4$ | 0.5 g |
| $MgSO_4.7H_2O$ | 0.2 g |
| $CaCl_2$ | 0.01 g |
| $FeSO_4$ | 0.005 g |
| $MnSO_4$ | 0.003 g |
| $Na_2MoO_4.2H_2O$ | 0.0025 g |
| Distilled water | 1.0 liter |
| Methanol | 5.0 ml. |

For the growth of *Microcyclus polymorphum* 0.01% yeast extract is added to the above medium. This medium may be solidified by the addition of 2% ($^w$/v) high purity agar (e.g. 'Oxoid' brand 'I.D.' agar).

Carbon source tests

Tests for the utilisation of the various carbon sources were performed in the above medium, adding 0.5% w/v of the carbon source under test in place of the methanol. Negative results of these tests indicate that no visible growth of the test organism on that particular carbon source occurred within 7 days incubation at 37° C. Positive results indicate that definite, visible growth of the organism did occur within 7 days, and that growth again occurred following subculture in that particular medium.

In the case of the *Pseudomonas methylotropha* strains, some period of adaption over several sub-cultures may result in growth on various other carbon sources. The results reported above for these strains refer to tests carried out without any prior adaption, as indicated in the above paragraph.

The carbon sources tested were:

methanol, ethanol, propanol, butanol, formate, acetate, propionate, butyrate pyruvate, oxalate, succinate, glutarate, adipate, methylamine, di-methylamine, ethylamine, sucrose, lactose, glucose, mannose, mannitol, ribose, ribitol, xylose, fructose, naphthalene, phenol, benzoate, hexane, hexadecane, aspartate, alanine, glycine, glutamate, arginine, serine.

3. Other tests.

The methods used for the following tests were as described in "Abstracts of Microbiological Methods" by V. B. D. Sherman, published by Wiley - Interscience, New York, 1969.

i. Oxidase test — method of Kovacs ii. Catalase test — as described in "Manual of Microbiological Methods" Published for Soc. of American Bacteriologists by McGraw-Hill, 1957.

iii. Nitrate reduction test — this was carried out in the above described methanol mineral salts medium, with the exception that sodium nitrate (0.5 g/l) was used as the nitrogen source instead of ammonium sulphate. With that exception the method was described in the Society of America Bacteriologists Manual of Microbiological Methods.

iv. Gelatin Hydrolysis — Manuroy's modification of Frazier's method was used.

v. Hugh & Liefson test — the original method of Hugh & Liefson was used.

xi. Lipase production — hydrolysis of Tween 80, using the method of Sierra.

xii. Lecithinase production — the method of Knight & Proom was used.

xiii. Urease production — the method of Koser was used, confirmed by the method of Monteverde et al using Buenos Aires Modified medium as described in "The Oxoid Manual" (3rd Edition), 1971, published by Oxoid Ltd, Southwark Bridge Road, London, SE1.

xiv. Hydrogen sulphide production — the method of Monteverde et al was used, as described in "The Oxoid Manual" (3rd Edition).

xv. Citrate utilisation — the method of Koser was used.

The process of the invention may be carried out as a batch culture, single stage continuous culture or multiple stage continuous culture process. The product of the process is a protein composition comprising bacterial cells together with other fermentation products for example amino acids, organic acids, nucleotides or their derivatives.

Suitable sources of assimilable carbon may be, for example, hydrocarbons or oxygenated hydrocarbons, polyhydric alcohols, carbohydrates (e.g. sucrose, glucose, fructose), sources of polymerised carbohydrates (for example starch) or naturally occurring or synthetic oils or fats. The carbon source is preferably an oxygenated hydrocarbon, alcohols such as methanol being particularly suitable. When the carbon source is methanol it may be supplied as the crude product of a methanol-synthesis process.

The culture medium preferably contains the carbon source e.g. methanol in proportions between 0.05% and 10% by weight, especially between 0.1% and 7.5% by weight.

The culture medium contains a nitrogen-containing compound which may suitably be ammonia, urea, an ammonium salt e.g. $(NH_4)_2SO_4$ or a nitrate e.g. $KNO_3$, preferably ammonia or an ammonium salt. Preferably the nitrogen-containing compound is present in the medium in proportions between 0.001% and 3% of elementary nitrogen, especially between 0.01% and 1% by weight. In addition to the nitrogen-containing compound, the medium also contains inorganic sources of elements such as potassium, phosphorus, sulphur and magnesium. These elements may be included in the medium by adding thereto compounds such as, for example, potassiuim chloride, magnesium sulphate, potassium phosphates and phosphoric acid. It is preferred that the inorganic compounds containing these elements are added to the medium in amounts sufficient to provide the following weight percent ion concentrations:

| | |
|---|---|
| K⁺ | 0.01 to 0.25 |
| Mg²⁺ | 0.001 to 0.1 |
| PO₄³⁻ | 0.01 to 0.5 |
| SO₄²⁻ | 0.01 to 0.25 |

The culture medium may also contain trace amounts of ions of other metallic elements, such as, for example, calcium, copper, iron, cobalt or manganese (which may be added to the medium as salts such as chlorides or sulphates) and, particularly, sodium which may be added e.g. as a chloride, sulphate or phosphate, preferably in an amount which provides a weight percent ion concentration of 0.002 to 0.06. It may also contain minor organic nutrients such as, for example, yeast extract, corn steep liquor, peptone, vitamins, amino acids, or cottonseed meal.

A suitable culture medium (hereinafter referred to as Medium I) has the following composition (concentrations given by weight per litre except where stated):

| | |
|---|---|
| CH₃OH | 20.0 g |
| H₃PO₄ | 0.0165 molar |
| (NH₄)₂SO₄ | 9.0 g |
| MgSO₄.7H₂O | 1.05 g |
| FeSO₄.7H₂O | 5.0 mg |
| CuSO₄.5H₂O | 0.1 mg |
| H₃BO₃ | 0.07 mg |
| MnSO₄.4H₂O | 0.5 mg |
| ZnSO₄.7H₂O | 0.5 mg |
| Na₂MoO₄ | 0.1 mg |
| CaCl₂.2H₂O | 13.24 mg |
| CoCl₂.6H₂O | 0.1 mg |
| water | - to 1 liter |

In this medium the pH value is adjusted for growth by the addition of a 1:1 mixture of 4N KOH/4N NaOH.

In continuous culture processes, the medium into which an organism is inoculated may be designed such that any of the elemental nutrients, e.g. nitrogen, phosphorus, magnesium or iron, or the carbon source may be in such quantities as to be limiting to growth with respect to the other constituents of the medium. Use may be made of this fact in regulating the growth of a culture.

To start up a continuous culture process, an inoculum of the organism or organisms to be used is added to a medium containing the carbon source and other nutrients. The culture is allowed to grow as a batch culture and is substantially transferred to continuous culture conditions by commencing to feed the medium into a fermenter. During fermentation, medium continuously leaves the fermenter at a rate similar to that at which fresh medium enters. The concentration of the growth limiting nutrient is increased in stages, until the culture is in a steady state and the medium entering the fermenter has the desired composition for the fermentation process.

The limiting nutrient may be the nitrogen or phosphorus source or, preferably, the carbon source. It may also oscillate between any two or all three of these nutrients.

Preferably the pH of the medium in which fermentation takes place is maintained at a desired level by step-wise or continuous addition of a suitable pH control agent. Suitable agents include sodium hydroxide, potassium hydroxide, disodium hydrogen phosphate and ammonia, either free or in aqueous solution. Mixtures of these pH control agents may be used. Other suitable pH control agents include aqueous solutions of hydrogen chloride, sulphuric acid, phosphoric acid and nitric acid. Preferably the pH is controlled in both the batch and continuous processes to within half a pH unit of the desired pH level, preferably within the range 5.0 to 8.0, especially 5.8 to 7.6.

The optimum temperature for the growth of the micro-organism of the invention varies according to the organism used and is usually controlled to within one degree of the desired temperature preferably within the range 20°–50° C. Especially suitable temperatures for the operation of the process of the invention lie within the range 34°–45° C.

In both batch and continuous culture the dissolved oxygen partial pressure in the culture medium may be controlled to be within the range 3 mm to 600 mm Hg, and preferably 30 mm to 150 mm Hg. The partial pressure of carbon dioxide in the effluent gas is maintained within the range 0-150 mm Hg and preferably within the range 0–40 mm Hg. The process of the invention may be performed using any suitable type of fermenter. A very suitable fermenter for the operation of a continuous process is described in our co-pending UK patent application No. 35285/70. The protein composition is formed as a slurry in the fermenter and is separated by methods such as centrifuging and/or filtration and flocculation from the liquid phase which contains any other products, e.g. amino acids, formed. The protein composition may be dried to form protein supplement for use in human /or animal foods.

If desired, protein may be extracted from the protein composition and the extracted protein may be used as a supplement for human or animal foods. The invention is illustrated by the following Examples:

A. Pseudomonas methylotropha - batch culture experiments.

EXAMPLE 1

Strain WKM-3 (NCIB 10508)

An inoculum culture was prepared by adding 10 ml of sterile saline to a culture of the micro-organism growing on methanol mineral salts agar slopes (composition as described in the description of strains, above). A suspension of cells was prepared and the entire suspension was used to inoculate a seed flask (a 1 l Erlenmeyer flask) containing 100 ml of the same medium. The pH value of this medium was adjusted before inoculation to pH 6.8. This seed culture was then incubated on a shaking machine at a temperature of 37° C for 36 hours.

This culture was then used to inoculate a fermenter containing 2 l of the following medium, (concentrations given by weight per liter except where stated):

| | | | |
|---|---|---|---|
| CH₃OH | 5.0 g | H₃BO₃ | 0.07 mg |
| H₃PO₄ | 0.0165 molar | MnSO₄.4H₂O | 0.5 mg |
| (NH₄)₂SO₄ | 9.0 g | ZnSO₄.7H₂O | 0.5 mg |
| MgSO₄.7H₂O | 1.05 g | Na₂MoO₄ | 0.1 mg |
| FeSO₄.7H₂O | 5.0 g | CaCl₂.2H₂O | 13.24 mg |
| CuSO₄.5H₂O | 0.1 mg | CoCl₂.6H₂O | 0.1 mg |

The pH value of this medium was adjusted to pH 6.8 prior to inoculation. After inoculation of this medium with the seed culture, the culture in the fermenter was agitated and aerated, with the culture temperature automatically controlled at 37° C, and the culture pH value automatically controlled at pH 6.8. After approximately 36 hr. of growth a further addition of 5 g of methanol to each liter of culture was made, followed by a further addition of 5 g of methanol to each liter of culture after 40 hr. of growth, and a final addition of 5 g of methanol to each liter of culture after 44 hr. After a total period of 48 hr. of fermentation, the cells were harvested and dried, to yield from the 2 liters of culture 10.4 g of dried cells, containing 65% by weight crude protein (N × 6.25).

EXAMPLE 2

Strain WKM-1 (NCIB 10509)

The procedure of Example 1 was repeated. 9.5 g of dried cells were obtained. The protein content (N × 6.25) of the cells was 68% by weight.

EXAMPLE 3

Strain SE(NCIB 10513)

The procedure of Example 1 was repeated. 10.6 g of dried cells were obtained. The crude protein content (N × 6.25) of the cells was 67% by weight.

EXAMPLE 4

Strain SF (NCIB 10514)

The procedure of Example 1 was repeated. 12.3 g of dried cells were obtained. The crude protein content of the cells (N × 6.25) was 62% by weight.

EXAMPLE 5

Strain As-1 (NCIB 10515)

The procedure of Example 1 was repeated. 11.6 g of dried cells were obtained. The crude protein content (N × 6.25) of the cells was 67% by weight.

EXAMPLE 6

Strain AS-1 (NCIB 10515)

The experiment was performed substantially as described in EXAMPLES 1 & 5. After harvesting the cells when the fermentation was complete, the culture supernatant was analysed for the presence of free amino-acids in the supernatant, using an automatic amino-acid analyser. The following amino acids were found in the quantities given:

| | | |
|---|---|---|
| glutamic acid | - | 135 mg/l |
| alanine | - | 32 mg/l |
| Valine | - | 111 mg/l |
| iso-leucine | - | 53 mg/l |
| leucine | - | 40 mg/l |
| lysine | - | 20 mg/l |

EXAMPLE 7

Strain MP4 (NCIB 10592)

The experiment was performed in shake-flask cultures as follows: An inoculum culture was prepared by adding 10 ml of sterile mineral salts solution to a slope culture of the micro-organism growing on methanol mineral salts agar slopes (composition as described in the description of strains above). A suspension of cells was prepared and the entire suspension was used to inoculate a 1 liter Erlenmeyer flask containing 200 ml of the same methanol mineral salts (0.5% w/v methanol). The pH value of this medium was adjusted prior to inoculation to pH 6.8. This culture was then incubated on a shaking machine at a temperature of 37° C for 24 hours. The cells were then harvested by centrifugation, and dried to give 0.171 g dry weight of cells from the 200 ml culture. The cells contained 62% by weight of crude protein (N × 6.25).

EXAMPLE 8

Strain F16/1 (NCIB 10593)

The procedure of Example 7 was repeated. 0.222 g of dried cells were obtained. The protein content of the cells was 66% by weight (N × 6.25).

EXAMPLE 9

Strain F16/2 (NCIB 10594)

The procedure of example 7 was repeated. 0.182 g of dried cells were obtained. The crude protein content of the cells (N × 6.25) was 69% by weight.

EXAMPLE 10

Strain MP1/Sh/37/1 (NCIB 10595)

The procedure of Example 7 was repeated. 0.270 g of dried cells were obtained. The protein content of the cells (N × 6.25) was 64% by weight.

EXAMPLE 11

Strain 28/D/37 (NCIB 10596)

The procedure of Example 7 was repeated. 0.240 g of dried cells were obtained. The protein content of the cells was 67% by weight (N × 6.25).

B. Pseudomonas methylotropha - continuous culture experiments

EXAMPLE 12

Strain MP4 (NCIB 10592)

Biomass was produced by culturing the bacterium in a carbon limited continuous culture process at a temperature of 40° C. The culture was aerated and agitated and the pH value was automatically controlled at pH 6.8. Foaming was controlled by automatic programmed additions of silicone oil. The experiment was performed as follows:

A seed batch culture of the organism was initially grown as described in Example 7. This seed culture after 24 hours growth was used to inoculate a fermenter containing 2.0 liters of medium II having the following compositions:

| | |
|---|---|
| Methanol | 10.0 g/l |
| $(NH_4)_2SO_4$ | 1.15 g/l |
| $H_3PO_4$ | 0.0066 molar |
| $MgSO_4.7H_2O$ | 0.42 g/l |
| $FeSO_4.7H_2O$ | 5.0 mg/l |
| $CuSO_4.5H_2O$ | 0.1 mg/l |
| $H_3BO_3$ | 0.07 mg/l |
| $MnSO_4.7H_2O$ | 0.5 mg/l |
| $ZnSO_4.7H_2O$ | 0.5 mg/l |
| $Na_2MoO_4$ | 0.1 mg/l |
| $CaCl_2.2H_2O$ | 13.2 mg/l |
| $CoCl_2.6H_2O$ | 0.1 mg/l |

The pH of this medium was adjusted to pH 6.8 by the addition of a 1:1 mixture of 4N KOH:4N NaOH. After inoculation of medium II with the seed culture, the culture in the fermenter was agitated and aerated, with the culture temperature automatically controlled at 40° C, and the culture pH automatically controlled at pH 6.8.

The culture was allowed to grow as a batch culture for approximately 36 hours by which time methanol in the medium had been fully utilized by the micro-organisms, and the concentration of the methanol in the medium was near zero. About this time the culture was made continuous by commencing to feed medium to the culture continuously. The medium had the same composition as medium II and was fed into the culture in two parts. One part comprised the mineral salts, and the other was methanol as a 50% aqueous solution. The medium feed rate was such that the dilution rate was 0.1 hr$^{-1}$. The culture was then allowed to grow for approximately 24 hours so that it might obtain a stable carbon limited steady state. The cells were then continuously harvested and dried. The steady state cell dry weight was 4.1 g/l and the cell yield with respect to methanol was 0.41 g of dried cells per g of methanol utilised.

The dried cells had a crude protein content of 68% by weight (N × 6.25). The amino acid content of the cells expressed in terms of anhydro amino acids as a percentage of the total amino acid content is given in Table 1.

EXAMPLE 13

Strain F16/1 (NCIB 10593)

The procedure of Example 12 was repeated, except that the fermentation temperature was controlled at 37° C.

The steady-state cell dry weight was 3.8 g/l and the cell yield with respect to methanol was 0.38 g of dried cells per g methanol utilised. The dried cells had a crude protein content (N × 6.25) of 78% by weight. The amino acid content of the cells is given in Table 1.

EXAMPLE 14

Strain F16/2 (NCIB 10594)

Example 13 was repeated using this strain. The steady state dry weight was 3.7 g/l and the cell yield with respect to methanol was 0.37 g dried cells per g of methanol utilised. The dried cells had a crude protein content of 76% by weight (N × 6.25).

EXAMPLE 15

Strain MP1/Sh/37/1 (NCIB 10595)

Example 13 was repeated using this strain. The steady state cell dry weight was 3.7 g/l and the cell yield with respect to methanol was 0.37g. The dried cells had a crude protein content of 76% by weight (N × 6.25). The amino acid content of the cells is shown in Table 1.

EXAMPLE 16

Strain 28/D/37 (NCIB 10596)

Example 13 was repeated using this strain. The steady state cell dry weight was 3.8 g/l and the cell yield with respect to methanol was 0.38 g of dried cells per g of methanol utilised. The dried cells had a crude protein content of 78% by weight (N × 6.25). The amino acid content of the cells is given in Table 1.

EXAMPLE 17

Strain As-1 (NCIB 10515)

Biomass was produced by culturing the bacterium in a carbon limited continuous culture process at a temperature of 37° C. The culture was aerated and agitated and the pH was automatically controlled at a pH value of 6.8. Foaming was controlled by automatic programmed additions of silicone oil. The experiment was performed as follows:

Seed cultures of the organism were initially grown as described in the first paragraph of Example 1 to provide an inoculum of 0.5 g dry wt/l. These seed cultures were then used to inoculate a fermenter containing 2.0 liters of medium 111 having the following composition:

| | |
|---|---|
| CH$_3$OH | 3.0 g/l |
| H$_3$PO$_4$ | 0.0099 M |
| MgSO$_4$.7H$_2$O | 0.67 g/l |
| Na$_2$SO$_4$ | 0.03 mg/l. |
| K$_2$SO$_4$ | 2.5 mg/l. |
| FeSO$_4$.7H$_2$O | 5.0 mg/l. |
| CuSO$_4$.5H$_2$O | 0.1 mg/l |
| H$_3$BO$_3$ | 0.07 mg/l |
| MnSO$_4$.7H$_2$O | 0.5 mg/l |
| ZnSO$_4$.7H$_2$O | 0.5 mg/l |
| Na$_2$MoO$_4$ | 0.1 mg/l |
| CaCl$_2$2H$_2$O | 13.2 mg/l |
| CoCl$_2$6H$_2$O | 0.1 mg/l |

The pH of this medium was adjusted to pH 6.8 by the controlled addition of gaseous ammonia. After inoculation of medium III with the seed cultures, the culture in the fermenter was agitated and aerated, with the culture temperature automatically controlled at 37° C and the culture pH value automatically controlled.

The culture was allowed to grow as a batch culture for approximately one hour by which time methanol in the medium had been fully utilised by the micro-organisms and the concentration of the methanol in the medium was about zero. About this time methanol was fed to the culture continuously at a slowly increasing rate such that the culture was growth limited at all times by the concentration of methanol in the medium. When the rate of methanol feed reached approximately 10 g 1 liter after about two hours the culture was made continuous by commencing to feed medium to the culture continuously. The medium had the same composition as Medium III and was fed into the culture in two parts. One part comprised the mineral salts and the other methanol as a 50% aqueous solution. The medium feed rate was such that the dilution rate was 0.1 hr$^{-1}$. The cell yield with respect to methanol was 0.38 g dried cells per g methanol utilised. The dried cells had a crude protein (N × 6.25) content of 78% by weight. The amino acid content of the cells is given in Table 1.

EXAMPLE 18

Strain SE (NCIB 10513)

Example 17 was repeated using this strain. The steady state cell dry weight was 3.5 g/l and the cell yield with respect to methanol was 0.35 g dried cells per g methanol utilized. The dried cells had a crude protein (N × 6.25) content of 81% by weight. The amino acid content is given in Table 1.

EXAMPLE 19

Strain WKM 1 (NCIB 10509)

Example 17 was repeated using this strain. The steady state dry weight was 2.7 g/l and the cell yield with respect to methanol was 0.27 g of dried cells per g of methanol utilised. The dried cells had a crude protein content (N × 6.25) of 88% by weight. The amino acid content of the cells is given in Table 1.

EXAMPLE 20

Strain SF (NCIB 10514)

Example 17 was repeated using this strain. The steady state cell dry weight was 3.4 g/l and the cell yield with respect to methanol was 0.34 g of dried cells per g of methanol utilised. The dried cells had a crude protein content (N × 6.25) of 77% by weight. The amino acid content of the cells is given in Table 1.

C. Microcyclus polymorphium strain Pla 5 (NCIB 10516)

EXAMPLE 21

Continuous Culture

Example 17 was repeated using strain Pla5. The experimental conditions were the same except that a carbon limited steady state was established at a dilution rate of 0.05 $hr^{-1}$. Additionally the medium contained 0.05% "DIFCO" Brand yeast extract.

The steady state cell dry weight was 2.2 g/l and the cell yield with respect to methanol was 0.22 g of dried cells per g of methanol utilised. The dried cells had a crude protein content (N × 6.25) of 87% by weight. The amino acid content of the cells is given in Table 1.

EXAMPLE 22

Batch culture

Using strain Pla5 an experiment was performed substantially as described in EXAMPLE 1. However, in this case the seed culture was grown for 48 hr. and in the fermentation further additions of methanol were made at different times. The first addition of a further 5 g of methanol to each liter of culture was made after 48 hr., the second addition after 56 hr. and the last addition after 64 hr. The cells were harvested and dried after a total fermentation time of 72 hr. to yield 9.6 g from the 2 l culture. The protein content (N × 6.25) of the cells was 67.5% by weight of protein.

D. Hyphomicrobium variable strain S/30/4 (NCIB 10517)

EXAMPLE 23

Batch Culture

Using strain S/30/4 an experiment was performed substantially as described in EXAMPLE 1. However, in this experiment the seed culture was grown for 72 hr. and in the fermentation further additions of methanol were made at different times. The first addition of a further 5 g of methanol to each liter of culture was made after 54 hr., the second addition after 64 hr., and the final addition after 74 hr. The incubation temperature in all cases in this example was 30° C. The cells were harvested and dried after a total fermentation time of 96 hr. to yield 10.7 g of dried cells from the 2 l culture. The protein content (N × 6.25) of the dried cells was 70% by weight.

EXAMPLE 24

Continuous Culture

Example 17 was repeated using strain S/30/4. The experimental conditions were the same except that a carbon limited steady state was established at a dilution rate of 0.05 $hr^{-1}$ with a methanol concentration in the inflowing medium of 5 g/l. The steady state cell dry weight was 1.5 g/l and the cell yield with respect to methanol was 0.3 g of dried cells per g of methanol utilised. The dried cells had a crude protein content (N × 6.25) of 80% by weight. The amino acid content of the cells is given in Table 1.

E. Pseudomonas rosea - Batch culture experiments

EXAMPLE 25

Strain MA2/3 (NCIB 10597)

The experiment was performed in shake-flask cultures as follows:

An inoculum culture was prepared by adding 10 ml of sterile mineral salts solution to a slope culture of the micro-organism growing on methanol mineral salts agar slopes (composition as described above in tests for identification of strains). A suspension of cells was prepared and the entire suspension was used to inoculate a 1 liter Erlenmeyer flask containing 200 ml of the same methanol mineral salts (0.5% w/v methanol). The pH value of this medium was adjusted prior to inoculation to pH 6.8. This culture was then incubated on a shaking machine at a temperatuare of 37° C for 24 hours. The cells were then harvested by centrifugation, and dried to give 0.227 g dry weight of cells from the 200 ml culture. The cells contained 55% by weight of crude protein (N × 6.25).

EXAMPLE 26

Strain BDD/3 (NCIB 10598)

The procedure of Example 25 was repeated. 0.226 g of dry weight of cells were obtained. The protein content of the cells was 58% by weight (N × 6.25).

EXAMPLE 27

Strain MA3D/1 (NCIB 10599)

The procedure of Example 25 was repeated. 0.221 g dry weight of cells were obtained. The protein content of the cells was 53% by weight (N × 6.25).

EXAMPLE 28

Strain Mw4/4(NCIB 10600)

The procedure of Example 25 was repeated. 0.224 g dry weight of cells were obtained. The protein content of the cells was 55% by weight (N × 6.25)

EXAMPLE 29

Strain MPID/2 (NCIB 10601)

The procedure of Example 25 was repeated. 0.202 g dry weight of cells were obtained. The protein content of the cells was 54% by weight (N × 6.25).

EXAMPLE 30

Strain MP3D/2 (NCIB 10602)

The procedure of Example 25 was repeated. 0.207 g dry weight of cells were obtained. The protein content of the cells was 56% by weight (N × 6.25).

EXAMPLE 31

Strain MP1/2 (NCIB 10603)

The procedure of Example 25 was repeated. 0.200 dry weight of cells were obtained. The protein content of the cells was 54% by weight (N × 6.25).

EXAMPLE 32

Strain MA2/2 (NCIB 10604)

The procedure of Example 25 was repeated. 0.225 g dry weight of cells were obtained. The protein content of the cells was 58% by weight (N × 6.25)

EXAMPLE 33

Strain 20/D(NCIB 10605)

The procedure of Example 25 was repeated. 0.220 g dry weight of cells were obtained. The protein content of the cells was 57% by weight (N × 6.25).

EXAMPLE 34

Strain MA1/5 (NCIB 10606)

The procedure of Example 25 was repeated. 0.161 g dry weight of cells was obtained. The protein content of the cells was 61% by weight (N × 6.25).

EXAMPLE 35

Strain MA3D/3 (NCIB 10607)

The procedure of Example 25 was repeated. 0.156 g dry weight of cells was obtained. The protein content of the cells was 63% by weight (N × 6.25).

EXAMPLE 36

Strain BDD/2(NCIB 10608)

The procedure of Example 25 was repeated. 0.188 g dry weight of cells were obtained. The protein content of the cells was 61% by weight (N × 6.25).

EXAMPLE 37

Strain MP1(NCIB 10609)

The procedure of Example 25 was repeated. 0.217 g dry weight of cells was obtained. The protein content of the cells was 59% by weight (N × 6.25).

EXAMPLE 38

Strain ChD(NCIB 10610)

The procedure of Example 25 was repeated. 0.210 g dry weight of cells was obtained. The protein content of the cells was 64% by weight (N × 6.25).

EXAMPLE 39

Strain WS (NCIB 10611)

The procedure of Example 25 was repeated. 0.250 g dry weight of cells were obtained. The protein content of the cells was 64% by weight (N × 6.25).

EXAMPLE 40

Strain MP3 (NCIB 10612)

The procedure of Example 25 was repeated. 0.209 g dry weight of cells were obtained. The protein content of the cells was 59% by weight (N × 6.25).

F. Pseudomonas Rosea - Continuous culture experiments

EXAMPLE 41

Strain MP1 (NCIB 10609)

Example 12 was repeated using Strain MP1. The experimental conditions were the same except that the experiment was carried out at 37° C, the culture was allowed to grow as a batch culture for 48 hours and after the culture had been made continuous it was allowed to grow for approximately 36 hours to allow it to obtain a stable steady state. The steady state cell dry weight was 3.38 g/l and the cell yield with respect to methanol was 0.338 g of dried cells per g of methanol utilised. The dried cells had a crude protein content of 68% by weight (N × 6.25). The amino acid content of the cells is given in Table 1.

EXAMPLE 42

Strain MP3 (NCIB 10612)

Example 41 was repeated using this strain. The steady state cell dry weight obtained was 3.53 g/l and the cell yield with respect to methanol was 0.353 g of dried cells per g of methanol utilised. The dried cells had a crude protein content of 69% by weight (N × 6.25). The amino acid content of the cells is given in Table 1.

EXAMPLE 43

Strain ChD(NCIB 10610)

Example 41 was repeated using this strain. The steady state cell dry weight obtained was 3.25 g/l and the cell yield with respect to methanol was 0.325 g of dried cells per g of methanol utilised. The dried cells had a crude protein content of 75% by weight (N × 6.25). The amino acid content of the cells is given in Table 1.

EXAMPLE 44

Strain WS(NCIB 10611)

Example 41 was repeated using this strain. The steady state cell dry weight obtained was 3.25 g/l and the cell yield with respect to methanol was 0.325 g of dried cells per g of methanol utilised. The dried cells had a crude protein content of 75% by weight (N × 6.25)

EXAMPLE 45

Strain MA2/3(NCIB 10597)

Example 41 was repeated using this strain. The steady state cell dry weight obtained was 3.16 g/l and the cell yield with respect to methanol was 0.316 g of dried cells per g of methanol utilised. The dried cells had a crude protein content of 72% by weight (N × 6.25)

EXAMPLE 46

Strain BDD/3(NCIB 10598)

Example 41 was repeated using this strain. The steady state cell dry weight was 3.42 g/l and the cell yield with respect to methanol was 0.342 g of dried cells per g of methanol utilised. The dried cells had a crude protein content of 74% by weight (N × 6.25).

EXAMPLE 47

Strain MA3D/1 (NCIB 10599)

Example 41 was repeated using this strain. The steady state cell dry weight was 3.30 g/l and the cell yield with respect to methanol was 0.330 g of dried cells per g of methanol utilised. The dried cells had a crude protein content of 68% by weight (N × 6.25).

EXAMPLE 48

Strain MW4/4(NCIB 10600)

Example 41 was repeated using this strain. The steady state cell dry weight was 2.94 g/l and the cell yield with respect to methanol was 0.294 of dried cells per g of methanol utilised. The dried cells had a crude protein content of 71% by weight (N × 6.25).

EXAMPLE 49

Strain MP1D/2 (NCIB 10601)

Example 41 was repeated using this strain. The steady state cell dry weight was 3.71 g/l and the cell yield with respect to methanol was 0.371 g of dried cells per g of methanol utilised. The dried cells had a crude protein content of 71% by weight. (N × 6.25).

EXAMPLE 50

Strain MP1/2(NCIB 10603)

Example 41 was repeated using this strain. The steady state cell dry weight was 3.02 g/l and the cell yield with respect to methanol was 0.302 g of dried cells per g of methanol utilised. The dried cells had a crude protein content of 68% by weight. (N × 6.25)

EXAMPLE 51

Strain MA2/2(NCIB 10604)

Example 41 was repeated using this strain. The steady state cell dry weight was 2.71 g/l and the cell yield with respect to methanol was 0.271 g of dried cells per g of methanol utilised. The dried cells had a crude protein content of 75% by weight (N × 6.25).

EXAMPLE 52

Strain 20/D (NCIB 10605)

Example 41 was repeated using this strain. The steady state cell dry weight was 3.69 g/l and the cell yield with respect to methanol was 0.369 g of dried cells per g of methanol utilised. The dried cells had a crude protein content of 67% by weight (N × 6.25).

EXAMPLE 53

Strain MA1/5(NCIB 10606)

Example 41 was repeated using this strain. The steady state cell dry weight was 3.42 g/l and the cell yield with respect to methanol was 0.342 g of dried cells per g of methanol utilised. The dried cells had a crude protein content of 71% by weight (N × 6.25).

EXAMPLE 54

Strain MA3D/3(NCIB 10607)

Example 41 was repeated using this strain. The steady state cell dry weight was 3.12 g/l and the cell yield with respect to methanol was 0.312 g of dried cells per g of methanol utilised. The dried cells had a crude protein content of 74% by weight. (N × 6.25)

EXAMPLE 55

Strain BDD/2 (NCIB 10608)

Example 41 was repeated using this strain. The steady state cell dry weight was 3.62 g/l and the cell yield with respect to methanol was 0.362 g of dried cells per g of methanol utilised. The dried cells had a crude protein content of 74% by weight. (N × 6.25).

EXAMPLE 56

Feeding trial on chickens.

The trial was carried out using 3 groups of chickens. For the first 10 days all groups were fed 'promine' diet 1 comprising: assay soyabean meal 21.7% (91% of crude protein in diet), d 1 methionine 0.464%, whey 2.5%, minerals 6.75%, vitamins 2.0%, ethoxyquin 0.015%, maize oil 8.0%, dextrose 40.0% corn starch 18.391% and glycine 0.2%. For the next 7 days diet 1 was continued to one group whilst the other groups were fed diets 2 and 3 which consisted of the 'promine' diet into which dried *Pseudomonas Methylotropha* protein composition and dried bakers yeast respectively had been substituted to form 25% of the crude protein in the diet. The results are set out below:

RESULTS

| Diet | Average Live weight gain (gms) | Average Feed intake (g) | Feed conversion ratio: gm. live wt. gain gm feed intake |
|---|---|---|---|
| 1 | 87.6 | 150 | 0.585 |
| 2 | 95.3 | 160 | 0.595 |
| 3 | 85.0 | 167 | 0.508 |

As may be seen the feed conversion ratio obtained using the composition of the invention compared favourably with those obtained using the other sources of protein tested.

TABLE 1

| AMINO ACID | Anhydro amino acid as % of total anhydro amino acid content EXAMPLE NOS. | | | | | |
|---|---|---|---|---|---|---|
| | 17 | 18 | 19 | 20 | 21 | 24 |
| Aspartic Acid | 11.1 | 11.3 | 11.5 | 12.0 | 8.5 | 11.1 |
| Threonine | 5.4 | 5.1 | 5.5 | 5.1 | 4.4 | 4.7 |
| Serine | 3.9 | 3.4 | 3.6 | 3.5 | 3.5 | 3.4 |
| Glutamic Acid | 12.3 | 12.5 | 12.3 | 12.8 | 12.7 | 13.4 |
| Proline | 4.5 | 3.9 | 5.3 | 4.2 | 5.8 | 5.1 |
| Glycine | 5.7 | 6.4 | 6.7 | 6.3 | 5.0 | 5.9 |
| Alanine | 7.7 | 8.1 | 8.3 | 7.8 | 7.7 | 7.0 |
| Valine | 6.2 | 6.6 | 6.4 | 6.9 | 5.8 | 6.1 |
| Methionine | 3.5 | 3.4 | 3.3 | 2.7 | 2.2 | 3.1 |
| Isoleucine | 5.7 | 5.6 | 5.6 | 5.8 | 5.5 | 5.0 |
| Leucine | 9.0 | 8.8 | 8.5 | 9.1 | 9.9 | 7.7 |
| Tyrosine | 4.2 | 4.2 | 4.2 | 3.6 | 5.6 | 4.5 |
| Phenylalanine | 4.8 | 4.9 | 4.0 | 4.6 | 5.6 | 5.0 |
| Lysine | 8.1 | 7.7 | 7.2 | 7.7 | 7.0 | 8.2 |
| Histidine | 2.4 | 2.4 | 2.3 | 2.0 | 2.2 | 2.7 |
| Arginine | 5.8 | 5.7 | 5.1 | 5.9 | 8.5 | 7.1 |
| Half-cystine | 0.6 | 0.5 | 0.5 | n.t. | n.t. | n.t. |
| Tryptophan | n.t | 2.0 | n.t. | n.t. | n.t. | n.t. |

TABLE 1-continued

| AMINO ACID | Anhydro amino acid as % of total anhydro amino acid content EXAMPLE NOS. | | | | | |
|---|---|---|---|---|---|---|
| Total Anhydro Amino Acids as % of dry matter | 56.4 | 58.1 | 61.1 | 55.2 | 41.9 | 50.7 |
| | 12 | 15 | 16 | 13 | 41 | 42 | 43 |
| Aspartic Acid | 10.7 | 10.5 | 10.9 | 10.6 | 10.1 | 10.1 | 10.0 |
| Threonine | 5.4 | 5.5 | 6.0 | 5.9 | 4.7 | 5.1 | 5.3 |
| Serine | 4.9 | 4.4 | 4.7 | 4.2 | 4.2 | 3.5 | 4.3 |
| Glutamic Acid | 12.2 | 12.5 | 12.3 | 11.5 | 13.5 | 12.4 | 12.5 |
| Proline | 5.0 | 5.2 | 5.2 | 5.4 | 5.9 | 6.3 | 5.6 |
| Glycine | 5.4 | 5.2 | 5.3 | 5.5 | 5.6 | 5.8 | 5.6 |
| Alanine | 7.8 | 7.8 | 8.2 | 7.5 | 8.2 | 7.4 | 7.3 |
| Valine | 6.4 | 6.0 | 6.0 | 6.5 | 6.0 | 6.5 | 6.5 |
| Methionine | 2.9 | 3.0 | 2.8 | 3.3 | 2.4 | 2.5 | 3.0 |
| Isoleucine | 5.5 | 5.2 | 4.6 | 5.2 | 4.0 | 4.6 | 5.3 |
| Leucine | 9.2 | 8.5 | 8.7 | 8.3 | 8.6 | 8.5 | 8.6 |
| Tyrosine | 4.2 | 4.6 | 4.8 | 4.8 | 3.5 | 4.1 | 4.2 |
| Phenylalanine | 4.4 | 5.0 | 4.5 | 4.8 | 4.0 | 5.0 | 4.4 |
| Lysine | 7.5 | 7.8 | 7.3 | 7.5 | 7.5 | 7.3 | 7.5 |
| Histidine | 2.2 | 2.7 | 2.3 | 2.5 | 2.1 | 2.4 | 2.5 |
| Arginine | 6.2 | 6.1 | 6.1 | 6.3 | 9.6 | 8.1 | 7.1 |
| Half-cystine | 0.6 | 0.6 | 0.7 | 0.6 | 0.8 | 0.8 | 0.7 |
| Tryptophan | 1.5 | 1.6 | n.t. | n.t. | 1.1 | 1.6 | 1.5 |
| Total Anhydro Amino Acids as % of dry matter | 49.0 | 55.6 | 50.0 | 58.4 | 46.7 | 54.3 | 53.2 | n.t. = not tested.
N.B. Amino acids determined by conventional Moore & Stein column chromatographic techniques. Half-cystine determined as cystic acid after performic oxidation. Tryptophan analysed using alkaline hydrolysis.

We claim:
1. A process for the microbiological production of a protein composition as the essential product which comprises aerobically culturing bacteria belonging to at least one methanol-utilizing strain of a species selected from the group consisting of Pseudomonas methylotropha, and Pseudomonas rosea, in an aqueous culture medium comprising methanol as a source of assimilable carbon and inorganic nutrients to produce said protein composition and recovering the protein composition so produced.

2. A process according to claim 1 wherein the bacteria belong to at least one strain selected from the group comprising NCIB Nos. 10508 to 10515 and 10592 to 10612.

3. A process according to claim 1 wherein the culture medium comprises a nitrogen source, selected from the group consisting of ammonia, an ammonium salt, urea and a nitrate, and inorganic sources of phosphorus, sulphur, magnesium, potassium and sodium.

4. A process according to claim 1 wherein the culture medium comprises ions of an element selected from the group consisting of calcium, copper, iron, cobalt and manganese.

5. A process according to claim 3 wherein the culture medium contains the carbon source in proportions between 0.05% and 10% by weight, the nitrogen source in proportions between 0.001% and 3% by weight of elementary nitrogen and the sources of phosphorus, sulphur, magnesium, potassium and sodium in amounts sufficient to provide the weight percent ion concentrations $PO_4^{3-}$ 0.01 to 0.5; $SO_4^{2-}$ 0.01 to 0.25; $Mg^{2+}$ 0.001 to 0.1; $K^+$ 0.01 to 0.25; $Na^+$ 0.002 to 0.06.

6. A process according to claim 1 wherein culturing is effected at a temperature within the range 20° to 50° C.

7. A process according to claim 6 wherein culturing is effected at a temperature within the range 34° to 45° C.

8. A process according to claim 3 wherein the species is *Pseudomonas methylotropha*.

9. A process according to claim 3 wherein the species is *Pseudomonas rosea*.

* * * * *